(12) United States Patent
Hirose

(10) Patent No.: US 10,544,061 B2
(45) Date of Patent: Jan. 28, 2020

(54) VANADIUM DIOXIDE

(71) Applicant: Murata Manufacturing Co., Ltd., Kyoto (JP)

(72) Inventor: Sakyo Hirose, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 0 days.

(21) Appl. No.: 15/686,254

(22) Filed: Aug. 25, 2017

(65) Prior Publication Data
US 2017/0349495 A1   Dec. 7, 2017

Related U.S. Application Data

(63) Continuation of application No. PCT/JP2016/055340, filed on Feb. 24, 2016.

(30) Foreign Application Priority Data

Feb. 27, 2015 (JP) .................. 2015-039343

(51) Int. Cl.
| | |
|---|---|
| C04B 35/495 | (2006.01) |
| C01G 31/02 | (2006.01) |
| G01N 25/48 | (2006.01) |
| C04B 35/499 | (2006.01) |
| C01G 23/00 | (2006.01) |
| C01G 31/00 | (2006.01) |
| H01J 37/28 | (2006.01) |

(52) U.S. Cl.
CPC .......... C04B 35/499 (2013.01); C01G 23/002 (2013.01); C01G 31/006 (2013.01); C01G 31/02 (2013.01); G01N 25/4866 (2013.01); H01J 37/28 (2013.01)

(58) Field of Classification Search
CPC ........................ C04B 35/495; C04B 35/499
See application file for complete search history.

(56) References Cited

U.S. PATENT DOCUMENTS

| | | | | |
|---|---|---|---|---|
| 9,868,672 | B2 * | 1/2018 | Hirose | .................. C04B 35/495 |
| 2010/0140568 | A1 * | 6/2010 | Tohma | .................. C01G 31/02 |
| | | | | 252/519.12 |
| 2017/0121229 | A1 | 5/2017 | Hirose | |

FOREIGN PATENT DOCUMENTS

| | | |
|---|---|---|
| JP | S61-220402 A | 9/1986 |
| JP | 2010-163510 A | 7/2010 |
| JP | 2010-223497 A | 10/2010 |
| WO | 2016/006338 A1 | 1/2016 |

(Continued)

OTHER PUBLICATIONS

Jing Du et al., Significant changes in phase-transition hysteresis for Ti-doped VO2 films prepared by polymer-assisted deposition, Solar Energy Materials and Solar Cells, Feb. 2011, vol. 95, No. 2, p. 469-475.

(Continued)

*Primary Examiner* — Karl E Group
(74) *Attorney, Agent, or Firm* — Pearne & Gordon LLP

(57) ABSTRACT

The present application provides vanadium dioxide doped with Ti, or vanadium dioxide further doped with other atoms selected from the group of W, Ta, Mo, and Nb. The vanadium dioxide of the present application is excellent in moisture resistance and in which deterioration of endothermic characteristics due to moisture is suppressed.

1 Claim, 4 Drawing Sheets

(56) References Cited

FOREIGN PATENT DOCUMENTS

WO          2016/009759 A1     1/2016
WO          2016/009760 A1     1/2016

OTHER PUBLICATIONS

Ikuya Takahashi et al., Thermochromic Properties of Double-Doped V02 Thin Films Prepared by a Wet Coating Method Using polyvanadate-based sols containing W and Mo or W and Ti, Japanese Journal of Applied Physics, Mar. 15, 2001, vol. 40, No. 3A, Part 1, p. 1391-1395.

Ikuya Takahashi et al., Thermochromic properties of double-doped V02 thin films fabricated from polyvanadate-based solutions, Proceedings of SPIE—The International Society for Optical Engineering, Jun. 18, 1999, vol. 3788, p. 26-33.

Meiping Jiang et al., Preparation of Ta—Ti co-doped V02 polycrystal thin film with high resistance temperature coefficient and without hysteresis, Advanced Materials Research, 2011, vol. 284-286, p. 2177-2181.

International Search Report dated Apr. 26, 2016 in PCT/JP2016/055340.

Written Opinion dated Apr. 26, 2016 in PCT/JP2016/055340.

\* cited by examiner

VANADIUM DIOXIDE

This is a continuation of International Application No. PCT/JP2016/055340 filed on Feb. 24, 2016 which claims priority from Japanese Patent Application No. 2015-039343 filed on Feb. 27, 2015. The contents of these applications are incorporated herein by reference in their entireties.

BACKGROUND

Technical Field

The present disclosure relates to vanadium dioxide or vanadium dioxide doped with other atoms.

On the background of the performance improvement for electronic devices in recent years, the number of electronic components has been increased, such as CPUs (central processing units), power amplifiers, FETs (field-effect transistors), ICs (integrated circuits), and voltage regulators which is heat sources, with the result that energy input has also been increased, thereby leading to a significant issue with heat generation. In particular, mobile devices such as smartphones and tablet terminals have, due to the heat, the problem of degrading the battery capacities, or seriously affecting the reliability of constituent electronic devices. Therefore, more advanced control of the temperatures in the devices has been required.

The heat generated from the heat sources as mentioned above is controlled by a cooling fan, a heat pipe, a heat sink, a thermal sheet, a Peltier element or the like as an existing heat management solution. For example, Patent JP 2010-223497 A describes a cooling system that has a heat sink in combination with a fan or a Peltier element (see JP 2010-223497 A).

However, the cooling system that has a heat sink in combination with a fan or a Peltier element as mentioned above has a relatively complex structure, and additionally increases device sizes, and it is hard to use, in particular, for thin devices such as smartphones and tablet terminals. Moreover, because of power consumption, the system is also disadvantageous from the viewpoint of low power consumption (how long the battery lasts).

Therefore, for the thin devices such as smartphones and tablet terminals, currently, there is only one means for temperature control with heat release through housings, and the escape of heat is achieved by thermally coupling the heat sources and the housings with thermal sheets or the like.

BRIEF SUMMARY

The heat dissipation through the housing as described above is limited because the surface area of the housing is limited. Therefore, the temperature of each heat source is measured, and when the temperature reaches a predetermined temperature or higher, the performance of a CPU or the like is limited (the heat generation itself is suppressed), thereby dealing with the temperature. More specifically, the increased temperatures of the housings may interfere with the performance of a CPU or the like. Obviously, this heat release through the housings, in other words, heat release through heat transfer to the whole devices, also transfers heat to batteries, which can also be considered as leading to deceases in battery capacity with the passage of time.

Therefore, the present inventor has considered vanadium oxide (specifically, vanadium dioxide) which is a ceramic material that absorbs heat by crystal-structural phase transition, magnetic phase transition, or the like, which is disposed near a heat source for an electronic device, thereby providing a cooling device that is usable without necessarily any power source. However, according to the study of the present inventor, it has become clear that general vanadium dioxide ($VO_2$) shows a good endothermic effect at the beginning, but the endothermic effect gradually decreases under high humidity environment. Accordingly, when vanadium dioxide is used as a cooling device, strong packaging is required to avoid contact with moisture (water vapor), which arises problems that the cost is increased and the shape and the like of the device are greatly restricted.

Accordingly, the present disclosure provides vanadium dioxide which is excellent in moisture resistance and in which deterioration of endothermic characteristics due to moisture is suppressed.

As a result of studying the problems described above, the present inventor has found that deterioration of endothermic characteristics under high humidity environment is caused by oxidation and hydroxylation due to exposure of vanadium dioxide to moisture. More specifically, vanadium exhibiting good endothermic characteristics is tetravalent ($V^{4+}$), which is oxidized and hydroxylated by water vapor and partly converted to pentavalent ($V^{5+}$), thereby deteriorating the endothermic characteristics. Thus, the present inventor has considered that stabilization of $V^{4+}$ is effective for improving moisture resistance, and as a result of further intensive studies, it has been found that Ti in which $Ti^{4+}$ with the same valence number is stable is doped in vanadium dioxide, whereby the moisture resistance is greatly improved.

According to a first aspect of the present disclosure, there is provided vanadium dioxide doped with Ti, or vanadium dioxide further doped with other atoms selected from the group consisting of W, Ta, Mo, and Nb, wherein when the other atoms are W, the content of the other atoms in parts by mole is more than 0 part by mole and 5 parts by mole or less, with respect to 100 parts by mole in total of vanadium, Ti and the other atoms, when the other atoms are Ta, Mo, or Nb, the content of the other atoms in parts by mole is more than 0 part by mole and 15 parts by mole or less, with respect to 100 parts by mole in total of vanadium, Ti and the other atoms, and the content of titanium in parts by mole is 2 parts by mole or more and 30 parts by mole or less, with respect to 100 parts by mole in total of vanadium, Ti and the other atoms.

According to a second aspect of the present disclosure, there is provided vanadium dioxide represented by formula:

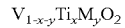

$$V_{1-x-y}Ti_xM_yO_2$$

wherein, M is W, Ta, Mo, or Nb, x is 0.02 or more and 0.3 or less, y is 0 or more, and y is 0.05 or less when M is W, and y is 0.15 or less when M is Ta, Mo, or Nb.

According to a third aspect of the present disclosure, a ceramic material containing the vanadium dioxide described above is provided.

According to a fourth aspect of the present disclosure, a cooling device including the vanadium dioxide described above or the ceramic material described above is provided.

According to a fifth aspect of the present disclosure, an electronic component including the cooling device described above is provided.

According to a sixth aspect of the present disclosure, an electronic device including the cooling device described above or the electronic component described above is provided.

According to the present disclosure, vanadium dioxide is doped with a predetermined amount of Ti, thereby making it possible to provide vanadium dioxide having high moisture resistance and excellent endothermic properties.

DETAILED DESCRIPTION

Figure 1:
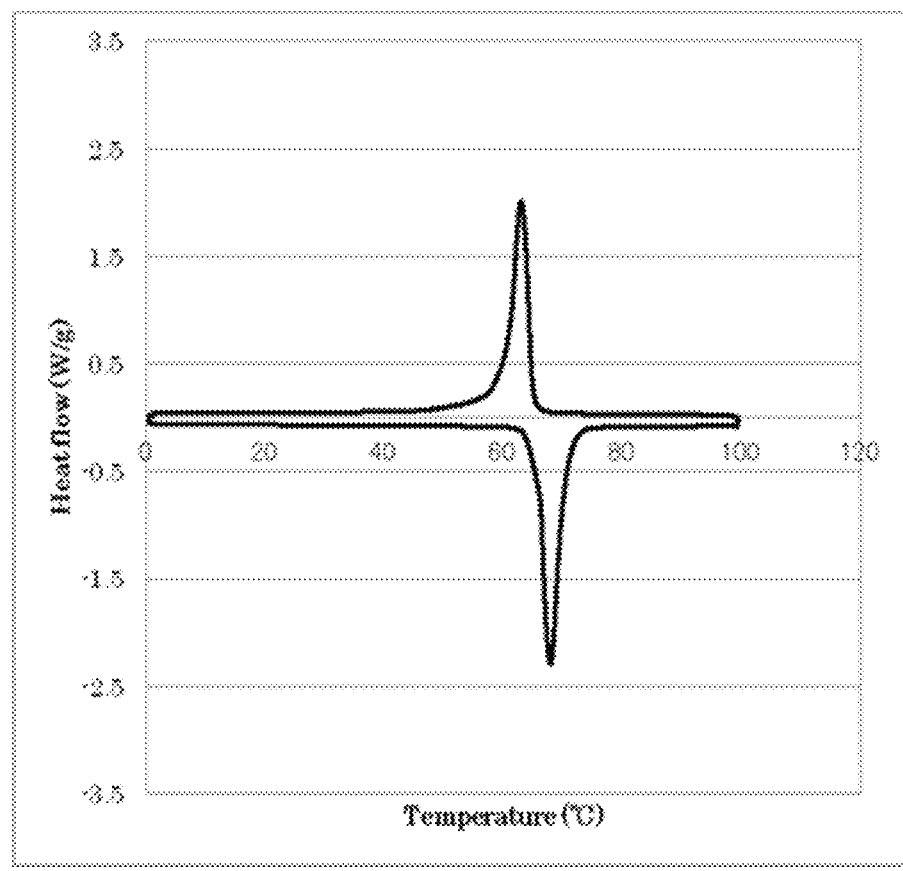
FIG. 1 shows the DSC measurement result for Sample No. 2 before the moisture resistance test.

The vanadium dioxide doped with Ti and vanadium dioxide further doped with other atoms of the present disclosure (hereinafter also collectively referred to as "the vanadium dioxide of the present disclosure") absorbs heat for latent heat. The vanadium dioxide of the present disclosure temporarily absorbs excess heat for latent heat, thereby achieving the temporal leveling of heat by releasing the heat absorbed when the temperature decreases, and thus making it possible to obtain a great cooling effect.

The vanadium dioxide of the present disclosure is usually used as a ceramic material containing the vanadium dioxide as a main component.

The "main component" means a component contained in the ceramic material, in an amount of 60 mass % or more, particularly 80 mass % or more, preferably 90 mass % or more, more preferably 95 mass % or more, still more preferably 98 mass % or more, for example, 98.0 mass % or more and 99.8 mass % or less or substantially 100%.

In the present disclosure, the "vanadium dioxide doped with Ti" represents vanadium oxide showing a corresponding crystal structure by X-ray structural analysis (typically using powder X-ray diffraction method). In the present specification, the "vanadium dioxide further doped with other atoms" represents vanadium dioxide doped with other atoms in addition to Ti, and vanadium oxide showing a corresponding crystal structure by X-ray structural analysis.

The vanadium dioxide of the present disclosure may contain impurities other than the vanadium dioxide doped with Ti or the vanadium dioxide further doped with other atoms. Examples of the impurities are not particularly limited, but include vanadium oxides other than those mentioned above, for example, undoped $VO_2$, $V_2O_3$, $V_2O_5$ and the like, and other ceramic materials, for example, glass, as well as Na, Al, Cr, Fe, Ni, Mo, Sb, Ca, Si and oxides thereof.

The amount of the impurities can be as small as possible, for example, 5 mass % or less, preferably 3 mass % or less, more preferably 1 mass % or less, further preferably 0.5 mass % or less, still more preferably 0.2 mass % or less, and most preferably substantially 0 mass % (that is, it contains substantially no impurities).

The content of Ti doped in the vanadium dioxide of the present disclosure is 2 parts by mole or more and 30 parts by mole or less, and preferably 5 parts by mole or more and 10 parts by mole or less, with respect to 100 parts by mole in total of vanadium, Ti, and the other atoms. Titanium atoms in such a range are doped in vanadium dioxide, whereby the moisture resistance of vanadium dioxide is greatly improved.

The other atoms are not particularly limited as long as they can be contained in the vanadium oxide as doping elements, but can be W, Ta, Mo and Nb, and more preferably W. It is noted that the other atoms are not necessarily essential components in the vanadium dioxide of the present disclosure and may not be contained. In this case, the vanadium dioxide of the present disclosure is "the vanadium dioxide doped with Ti".

When the other atoms are W, the content of other atoms in parts by mole can be more than 0 part by mole and 5 parts by mole or less, with respect to 100 parts by mole in total of vanadium, Ti, and the other atoms.

When the other atoms are Ta, Mo, or Nb, the content of other atoms in parts by mole can be more than 0 part by mole and 15 parts by mole or less, with respect to 100 parts by mole in total of vanadium, Ti, and the other atoms.

In one aspect, the vanadium dioxide of the present disclosure can be vanadium dioxide of a formula:

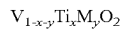

$$V_{1-x-y}Ti_xM_yO_2$$

wherein, M is W, Ta, Mo, or Nb, x is 0.02 or more and 0.3 or less, y is 0 or more, and y is 0.05 or less when M is W, and y is 0.15 or less when M is Ta, Mo, or Nb.

Herein, M corresponds to "other atoms", and is not necessarily an essential component, and the content of M in parts by mole may be 0. In this case, the compound of the above formula becomes vanadium dioxide doped only with titanium.

In an embodiment, x is 0.05 or more and 0.1 or less. By setting x to such a range, the moisture resistance of the vanadium dioxide of the present disclosure can be further improved.

In one embodiment, the vanadium dioxide of the present disclosure is a compound of the above formula wherein x is 0, that is, vanadium dioxide doped only with Ti.

In another embodiment, the vanadium dioxide of the present disclosure is a compound wherein y is more than 0 and M is W, that is, titanium and tungsten doped vanadium dioxide.

The temperature at which the vanadium dioxide of the present disclosure undergoes a phase transition is selected appropriately depending on the object to be cooled, the purpose of cooling, or the like, and for example, when the object to be cooled is a CPU, the vanadium oxide can undergo the phase transition at 20 to 100° C., and preferably 40 to 60° C. during temperature rising. The temperature at which the vanadium dioxide of the present disclosure undergoes a phase transition, that is, the temperature indicating the latent heat of the vanadium dioxide of the present disclosure, can be adjusted by adding (doping) other atoms, and adjusting the additive amount of the atoms.

The vanadium dioxide of the present disclosure has an initial latent heat amount of 35 J/g or more, more preferably 40 J/g or more, and further preferably 43 J/g or more. Also, the vanadium dioxide of the present disclosure has a latent heat amount of 30 J/g or more, more preferably 35 J/g or more, and further preferably 40 J/g or more, even after the moisture resistance test (storage at 85° C. and relative humidity of 85% for 500 hours). Even when exposed to moisture as described above, by having a high latent heat amount, it is not necessary to take measures against moisture when making it into a device, and the like, which is advantageous in cost, shape and the like. Further, by having a larger latent heat amount, a great cooling effect can be exhibited with a smaller volume, which is advantageous in terms of miniaturization. The "latent heat" herein represents the total amount of heat energy required when the phase of a substance is changed, and in the present specification, represents the generated/absorbed heat quantity associated with a solid-solid phase transition, for example, an electric/magnetic/structural phase transition.

The vanadium dioxide of the present disclosure can be particulates (powdery). The average particle size (D50: the particle size at the point of a cumulative value corresponding to 50% on a cumulative curve with the total volume regarded as 100% in regard to a particle size distribution obtained on a volume basis) of the core part of the vanadium dioxide of the present disclosure is not particularly limited, but for example, 0.1 μm or more and several hundred μm or less, specifically 0.1 μm or more and 900 μm or less, typically approximately 0.2 μm or more and 50 μm or less, and preferably 0.5 μm or more and 50 μm or less. The average particle size can be measured with the use of a laser diffraction-scattering type particle size-particle size distribution measurement system or an electron scanning microscope. The average particle size can be 0.2 μm or more from the viewpoint of ease of handling and moisture resistance, and preferably 50 μm or less from the viewpoint of being capable of finely forming.

The above-mentioned vanadium dioxide or ceramic material of the present disclosure can be formed into desired shapes, for example, a sheet, a block, and various other shapes. The forming method is not particularly limited, but compression, sintering, and the like can be used. In addition, the material may be mixed with a binder such as a resin, a rubber, a glass, or the like, and formed into the shapes. Furthermore, the material may be mixed with a fluid resin or the like to provide a paste.

The above-mentioned vanadium dioxide or ceramic material of the present disclosure may be partially or entirely coated with an insulating material, for example, resin, glass, or the like. The vanadium dioxide of the present disclosure is coated with an insulating material, whereby it is possible to directly install the vanadium dioxide of the present disclosure in the vicinity of a heat source where current can flow or on the circuit board.

As described above, the vanadium dioxide or ceramic material of the present disclosure can be suitably used as a cooling device, since the latent heat is large, that is, the endothermic amount is large, and the generated and absorbed heat is generated promptly.

Therefore, the present disclosure also provides a cooling device including the above-mentioned vanadium dioxide or ceramic material of the present disclosure.

The shape of the cooling device of the present disclosure is not particularly limited, and can be any shape.

In one embodiment, the cooling device of the present disclosure can have the shape of a block. The adoption of the shape of a block increases the overall volume, thereby making it possible to absorb a larger amount of heat. In addition, in another embodiment, the cooling device according to the present disclosure can have the shape of a sheet. The adoption of the shape of a sheet increases the surface area, thus making absorbed heat to be easily released to the outside. Further, the powder may be in a shape laminated with a metal foil, a sheet, or the like or wrapped.

The cooling device of the present disclosure may have other members, for example, a protective cover that protects the cooling device, a thermal conductive part such as a metal for enhancing thermal conductivity, an insulating sheet for ensuring insulation, a member (for example, an adhesive sheet, a pin, a claw, and the like) for installation in an electronic device, or the like.

In addition, the present disclosure also provides an electronic component including the cooling device of the present disclosure, and an electronic device including the cooling device or the electronic component.

The electronic component is not particularly limited, and examples thereof include components commonly used in electronic devices such as integrated circuits (ICs) such as a central processing unit (CPU), a power management IC (PMIC), a power amplifier (PA), a transceiver IC, and a voltage regulator (VR); light-emitting elements such as a light emitting diode (LED), an incandescent light bulb, and a semiconductor laser; components which can be a heat sources such as a field-effect transistors (FET); and other components, e.g., a lithium ion battery, a substrate, a heat sink, a housing, and the like.

The electronic device is not particularly limited, and examples thereof include a cellular phone, a smartphone, a personal computer (PC), a tablet terminal, a hard disc drive, and the like.

Although the present disclosure has been described above, the present disclosure is not limited to the above-described embodiments, and various modifications can be made.

EXAMPLES

The following materials were prepared as starting materials.

Vanadium Raw Material

Vanadium dioxide ($VO_2$, manufactured by Dalian Bolong New Material Co., Ltd.)

Added (Doped) Raw Materials

Titanium oxide ($TiO_2$)

Tungsten oxide ($WO_3$)

Tantalum oxide ($Ta_2O_5$)

Niobium oxide ($Nb_2O_5$)

Molybdenum oxide ($MoO_3$)

Each raw material was weighed so that the composition shown in following Table 1 was obtained, and dry formulated using an IKA mill. Thereafter, in an atmosphere of nitrogen/hydrogen/water or nitrogen/air/hydrogen/water, heat treatment was performed at 900° C. to 1100° C. while controlling the atmosphere so that the vanadium dioxide became stable. The atmosphere may be any atmosphere as long as the vanadium dioxide becomes stable, and the optimum conditions vary depending on the condition of the raw material, but here, the oxygen partial pressure was controlled to be in the range of $1\times10^{-8}$ MPa to $1\times10^{-11}$ MPa. Compositions of V, W, Ta, Nb, and Mo were determined for the resulting samples by ICP (high frequency inductively coupled plasma) emission spectroscopy. Further, it was confirmed by the powder X-ray diffraction method that the vanadium dioxide of the present disclosure was the main component.

Moisture Resistance Test

The temperature of the sample was swept in a nitrogen atmosphere at a heating rate of 10 K/min, from 0° C. to 100° C., and to 0° C., and the endothermic amount during temperature rising was measured by a DSC (differential scanning calorimetry) method. The endothermic amount during temperature rising was defined as an initial latent heat amount. Typically, the DSC measurement result for Sample No. 2 is shown in FIG. 1.

Figure 2:
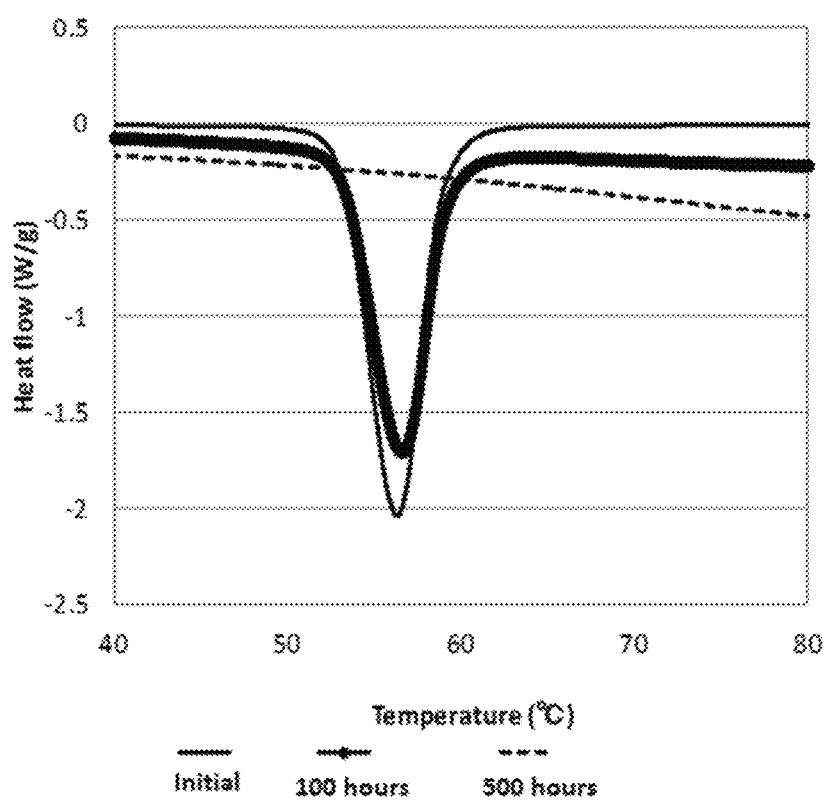
FIG. 2 shows the DSC measurement results for Sample No. 2 in the moisture resistance test.

The obtained powder sample was subjected to a moisture resistance test by leaving it in an environment of 85° C. and a relative humidity of 85% for 500 hours. Thereafter, the latent heat amount was again measured. Typically, the DSC measurement results (only for endothermic) for Sample No. 2 in the moisture resistance test are shown in FIG. 2.

The measurement results of the latent heat amount are shown in Table 1. The numbers marked with * are comparative examples.

TABLE 1

| Sample No. | Composition | Initial latent heat amount (J/g) | Latent heat amount after moisture resistance test (J/g) |
|---|---|---|---|
| 1* | $VO_2$ | 68.2 | — |
| 2* | $V_{0.995}W_{0.005}O_2$ | 50.2 | — |
| 3* | $V_{0.99}W_{0.01}O_2$ | 39.1 | — |
| 4* | $V_{0.99}Mo_{0.01}O_2$ | 38.2 | — |
| 5* | $V_{0.99}Nb_{0.01}O_2$ | 42.5 | — |
| 6* | $V_{0.99}Ta_{0.01}O_2$ | 40.1 | — |
| 7* | $V_{0.99}Ti_{0.01}O_2$ | 52.7 | — |
| 8 | $V_{0.98}Ti_{0.02}O_2$ | 49.2 | 32.1 |
| 9 | $V_{0.95}Ti_{0.05}O_2$ | 45.9 | 41.2 |
| 10 | $V_{0.9}Ti_{0.1}O_2$ | 43.4 | 42.2 |
| 11 | $V_{0.8}Ti_{0.2}O_2$ | 40.3 | 39.7 |
| 12 | $V_{0.7}Ti_{0.3}O_2$ | 36.5 | 35.5 |
| 13* | $V_{0.6}Ti_{0.4}O_2$ | 28.2 | 25.8 |
| 14 | $V_{0.895}Ti_{0.1}W_{0.005}O_2$ | 49.5 | 47.6 |
| 15 | $V_{0.85}Ti_{0.1}W_{0.05}O_2$ | 38.0 | 33.9 |
| 16 | $V_{0.895}Ti_{0.1}Mo_{0.005}O_2$ | 37.6 | 33.7 |
| 17 | $V_{0.75}Ti_{0.1}Mo_{0.15}O_2$ | 38.9 | 35.9 |
| 18 | $V_{0.895}Ti_{0.1}Ta_{0.005}O_2$ | 42.5 | 40.2 |
| 19 | $V_{0.75}Ti_{0.1}Ta_{0.15}O_2$ | 37.2 | 36.1 |
| 20 | $V_{0.895}Ti_{0.1}Nb_{0.005}O_2$ | 41.9 | 38.9 |
| 21 | $V_{0.75}Ti_{0.1}Nb_{0.15}O_2$ | 33.8 | 34.5 |

As shown in FIG. 1 and FIG. 2, the vanadium oxide of Sample No. 2 containing no titanium showed a large endothermic peak during temperature rising before the moisture resistance test, but in accordance with progress of the moisture resistance test, the endothermic peak declined, and the peak could not be confirmed after 500 hours. Therefore, when the sample after the moisture resistance test was examined by X-ray powder diffraction, it was found that the crystalline phase different from $V_{0.995}W_{0.005}O_2$ was the main, and it is presumed that the sample was changed to another substance due to moisture and the endothermic characteristic was lost.

As shown in Table 1, no endothermic peak could be confirmed in Sample Nos. 1 to 6 containing no titanium and Sample No. 7 with a titanium content of 0.01 parts by mole after the moisture resistance test. Further, in Sample No. 13 in which a titanium content was 0.4 parts by mole, the endothermic peak did not disappear even after the moisture resistance test, but because the titanium content was large, the latent heat amount was less than 30 J/g. On the other hand, Sample Nos. 8 to 12 and 14 to 21 having a titanium content of 0.02 to 0.3 parts by mole had a latent heat amount of 30 J/g or more even after the moisture resistance test, and it was confirmed that these samples had high latent heat amount and excellent moisture resistance. Although the above was tested in powder form, it was confirmed that even with a sintered body, deterioration occurs similarly with moisture although it occurs slowly.

Surface Observation

Furthermore, on behalf of the samples, the states of the particles of Sample Nos. 2 and 10 before and after the moisture resistance test were observed with a scanning electron microscope. The results for Sample No. 2 are shown in FIG. 3 (before moisture resistance test) and FIG. 4 (after moisture resistance test), and the results for Sample No. 10 are shown in FIG. 5 (before moisture resistance test) and FIG. 6 (after moisture resistance test).

Figure 3:
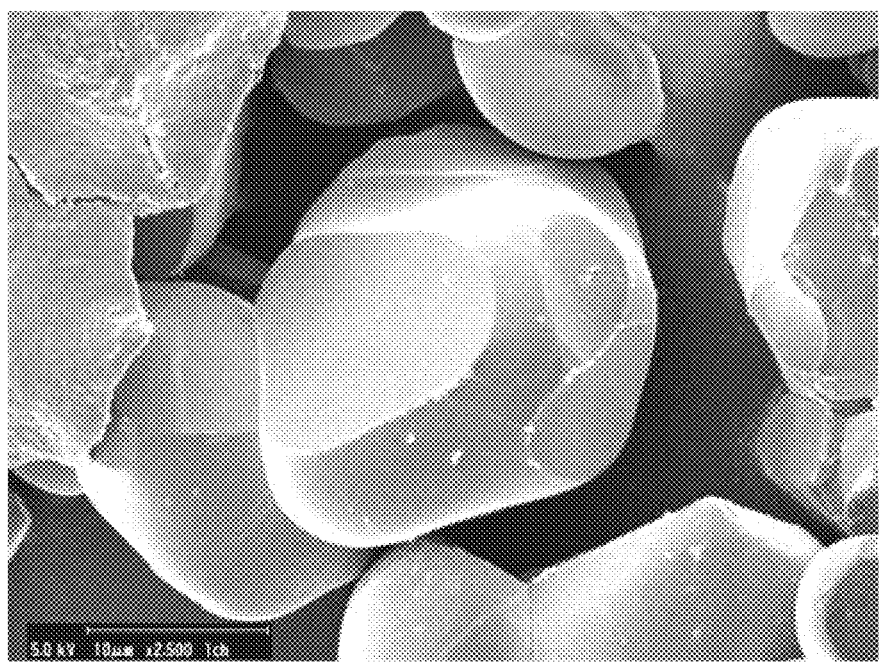
FIG. 3 shows the result of scanning electron microscope observation of Sample No. 2 before the moisture resistance test.
Figure 4:
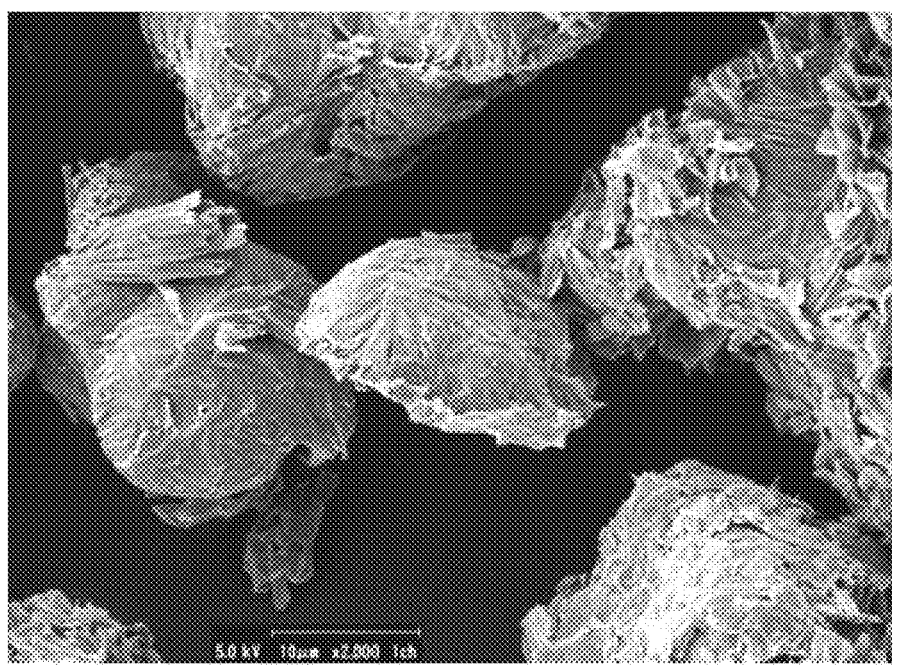
FIG. 4 shows the result of scanning electron microscope observation of Sample No. 2 after the moisture resistance test.
Figure 5:
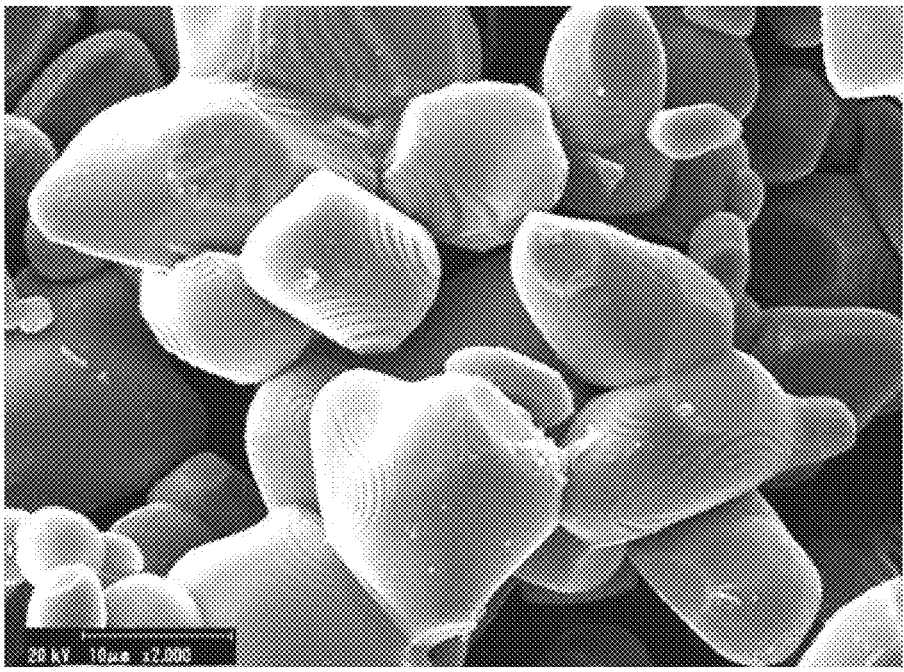
FIG. 5 shows the result of scanning electron microscope observation of Sample No. 10 before the moisture resistance test.
Figure 6:
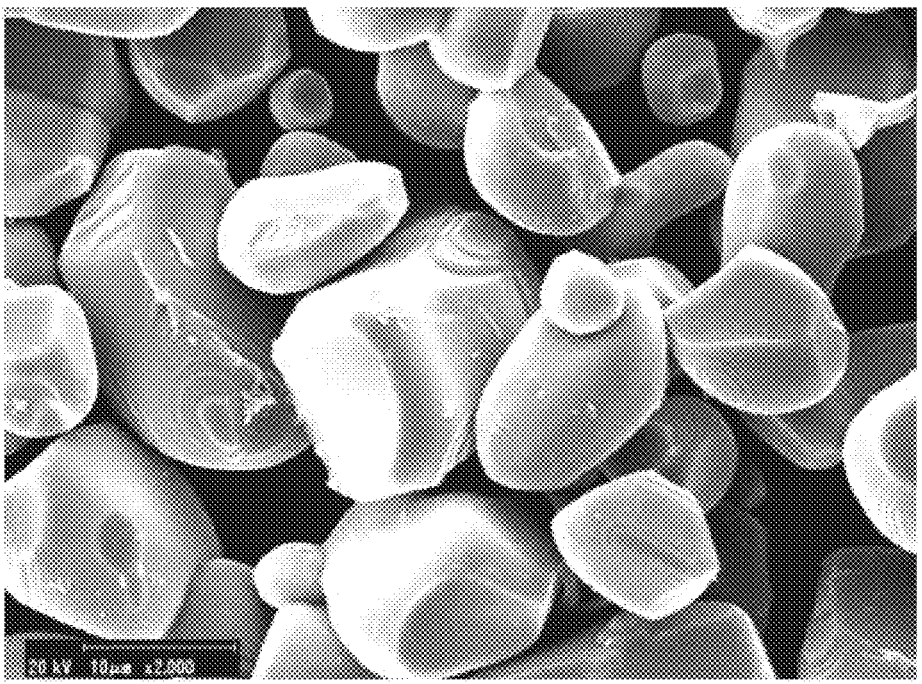
FIG. 6 shows the result of scanning electron microscope observation of Sample No. 10 after the moisture resistance test.

As shown in FIGS. 3 and 4, the particles of Sample No. 2, which are vanadium dioxide containing no titanium, have greatly changed in the surface state, and it is considered that hydroxylation and the like occurred due to moisture. On the other hand, as shown in FIGS. 5 and 6, the particles of Sample No. 10, which are the vanadium dioxide of the present disclosure, showed no significant change in the surface state before and after the moisture resistance test. This is considered to be due to the suppression of the reaction such as hydroxylation due to the improved moisture resistance.

Although the present disclosure is not bound by any theory, the reason that the moisture resistance is improved by being doped with Ti is considered as follows. Deterioration of vanadium dioxide due to moisture may be derived from instability of $V^{4+}$. It is considered that $V^{4+}$ in vanadium dioxide is likely to change to $V^{5+}$ by high humidity atmosphere that is an oxidizing atmosphere, and vanadium dioxide is subjected to oxidation or hydroxylation to deteriorate. It is considered that $V^{4+}$ was stabilized by solid solution of a proper amount of titanium dioxide stable in tetravalent ($Ti^{4+}$) in vanadium dioxide and oxidation from $V^{4+}$ to $V^{5+}$ could be suppressed in a high humidity atmosphere.

In the present specification, for the sake of convenience, the oxygen amount in the chemical formula is described as 2 (2 parts by mole of oxygen, with respect to 1 part by mole in total of vanadium, Ti and other atoms M), but as long as it is vanadium dioxide that can be crystal-structurally stably formed, slight deviation from 2 is permitted. This slight deviation is approximately 1.9 to 2.1 in VOx from the oxygen amount obtained from the chemical analysis result. Even in this case, it is possible to obtain vanadium dioxide which exhibits the same action and effect as the present disclosure and has high moisture resistance and excellent endothermic properties.

INDUSTRIAL APPLICABILITY

The cooling device of the present disclosure can be used as, for example, a cooling device of a small-size communication terminal which has a significant issue with countermeasures against heat.

The invention claimed is:

1. A paste for cooling comprising
   vanadium dioxide doped with Ti, or vanadium dioxide doped with Ti and other atoms selected from the group consisting of W, Ta, Mo, and Nb, wherein:
   when the other atoms are W, the content of the other atoms in parts by mole is more than 0 part by mole and 5 parts by mole or less, with respect to 100 parts by mole in total of vanadium, Ti and the other atoms,
   when the other atoms are Ta, Mo, or Nb, the content of the other atoms in parts by mole is more than 0 part by mole and 15 parts by mole or less, with respect to 100 parts by mole in total of vanadium, Ti and the other atoms, and the content of titanium in parts by mole is 2 parts by mole or more and 30 parts by mole or less, with respect to 100 parts by mole in total of vanadium, Ti and the other atoms, and a fluid resin.

* * * * *